United States Patent [19]

Jones et al.

[11] Patent Number: 4,681,112

[45] Date of Patent: Jul. 21, 1987

[54] MEDICAL INSTRUMENT INCLUDING ELECTRODES ADAPTED FOR RIGHT AND LEFT-HANDED USE

[75] Inventors: Paul W. Jones, Issaquah; Casey M. Bardue, Seattle, both of Wash.

[73] Assignee: Physio-Control Corporation, Redmond, Wash.

[21] Appl. No.: 914,004

[22] Filed: Oct. 1, 1986

Related U.S. Application Data

[63] Continuation-in-part of Ser. No. 689,741, Jan. 8, 1985.

[51] Int. Cl.$^4$ .............................................. A61N 1/00
[52] U.S. Cl. ................................. 128/419 D; 128/800
[58] Field of Search ............... 128/419 D, 419 P, 639, 128/783, 800, 801; 16/DIG. 12; 30/340, 341

[56] References Cited

U.S. PATENT DOCUMENTS

| | | | |
|---|---|---|---|
| 2,521 | 3/1842 | Coad | 128/800 |
| 2,327,874 | 8/1943 | De Jong | 128/800 |
| 3,022,878 | 2/1962 | Seibel et al. | 273/1 E |
| 3,196,877 | 7/1965 | Corbin | 128/800 |
| 3,670,736 | 6/1972 | Panico | 128/419 D |
| 4,023,573 | 5/1977 | Pantridge et al. | 128/419 D |

Primary Examiner—Henry J. Recla
Assistant Examiner—Randy Citrin
Attorney, Agent, or Firm—Christensen, O'Connor, Johnson & Kindness

[57] ABSTRACT

A medical instrument such as a defibrillator that includes first and second hand-held electrodes for applying an electric shock to a patient, wherein the two electrodes are respectively adapted for right and left-handed use. Each electrode comprises an elongated member (62) adapted for gripping by the fingers of an operator's hand, an actuator (26) positioned adjacent one end of the elongated member, and blocking means (52) positioned adjacent one side of the elongated member. The blocking means is adapted to hinder an operator from gripping the elongated member with one of the operator's hands while simultaneously positioning the thumb of that hand adjacent the actuator. The electrode is therefore adapted for either left-handed or right-handed use. The blocking means may comprise one sidewall (52) of a cup-shaped depression (50), and the elongated member may comprise a handle (62) spanning the cup-shaped depression in a direction parallel to the sidewall. The electrode may further include a lateral recess (102) to further isolate the operator's hand from the electrode element (66). A defibrillator having right and left-handed electrodes as described is therefore adapted for use with a preestablished polarity.

9 Claims, 3 Drawing Figures

MEDICAL INSTRUMENT INCLUDING ELECTRODES ADAPTED FOR RIGHT AND LEFT-HANDED USE

RELATED APPLICATIONS

This application is a continuation-in-part of application Ser. No. 689,741, filed Jan. 8, 1985, entitled Electrode Adapted for Right or Left-Handed Use.

FIELD OF THE INVENTION

The present invention relates to medical having hand-held electrodes.

BACKGROUND OF THE INVENTION

A defibrillator is a therapeutic instrument that is used to assist in curing certain cardiac irregularities, particularly ventricular and atrial fibrillation. The defibrillator is typically interconnected with a patient via a pair of paddle electrodes and associated conductors, and functions to apply a high energy pulse to the patient via the electrodes when appropriately triggered by an operator. A defibrillator is frequently used in conjunction with an ECG monitor that provides a display of a patient's ECG waveform and that may also be interconnected with the patient via a set of electrodes. In one type of prior physiological instrument, a combined defibrillator/ECG monitor is provided in which the electrodes normally used for defibrillation can be used to provide the ECG signal to the ECG monitor.

One common method of positioning defibrillator electrodes on a patient is referred to as the anterior/anterior technique. In this technique, one electrode is placed lateral to the upper sternum and below the right clavicle on the patient's right chest (the "sternum" position), and the second electrode is placed on the patient's lower left chest, usually just below and lateral to the cardiac apex (the "apex" position). The terms "right" and "left" are here used in relation to the patient. Since the operator will be facing the patient during defibrillation, the electrode in the sternum position will be held in the operator's left hand, and the electrode in the apex position will be held in the operator's right hand.

Defibrillation efficiency is generally considered to be unaffected by the polarity of the sternum and apex electrodes, i.e., an effective defibrillation shock can be applied regardless of whether the electrode in the sternum position is negative or positive with respect to the electrode in the apex position. Nevertheless, it is a long-standing convention in the health care field to apply a defibrillation pulse with the sternum electrode predominantly negative with respect to the apex electrode. The importance of this convention lies principally in the fact that the electrodes are often used as the source of an ECG signal. When the defibrillator electrodes are used to provide the ECG signal, use of the electrodes in preestablished apex and sternum positions ensures that the resulting ECG display or printout will not be inverted with respect to its normal form. An inverted ECG signal could conceivably be misinterpreted, particularly under emergency conditions. Most prior defibrillators have therefore included electrodes labeled with the terms "Sternum" and "Apex" to facilitate proper placement of the electrodes on the patient. However, labeling the electrodes does not guarantee that an operator will place them in their proper positions.

SUMMARY OF THE INVENTION

The present invention provides electrodes that are physically adapted for either right or left-handed use. When used with a defibrillator or other medical instrument, such electrodes facilitate operation of the instrument with the electrodes in preestablished positions or with preestablished polarity.

The present invention comprises a medical instrument such as a defibrillator that includes first and second electrodes, and means for applying an electric shock to a patient through the electrodes. Each electrode includes an elongated member adapted for gripping by the fingers of an operator's hand, an actuator positioned adjacent one end of the elongated member, and blocking means positioned adjacent one side of the elongated member. The blocking means of the first electrode is adapted to hinder an operator from gripping the elongated member with the operator's right hand and simultaneously positioning the thumb of that hand adjacent the actuator. The blocking means of the second electrode is adapted to hinder an operator from gripping the elongated member with the operator's left hand and simultaneously positioning the thumb of that hand adjacent the actuator. The first and second electrodes are therefore adapted for left-handed and right-handed use respectively by the operator. The blocking means may comprise one sidewall of a cup-shaped depression, and the elongated member may comprise a handle spanning the cup-shaped depression in a direction parallel to the sidewall, such that when the elongated member is gripped by the fingers of the operator's hand, the fingers are received in the cup-shaped depression. The electrode may further comprise a housing that includes the sidewall and a bottom wall, an electrode element underlying the bottom wall, and a lateral recess around a substantial portion of the periphery of the electrode to provide increased isolation of the operator's hand from the electrode element.

In many defibrillators, the apex (right hand) electrode is energized such that it is predominantly positive with respect to the sternum (left hand) electrode. However the opposite polarity could also be used within the scope of the present invention. In a defibrillator, the present invention helps to insure that the apex and sternum electrodes will in fact be used in the apex and sternum positions, respectively, thereby insuring the correct ECG polarity.

DETAILED DESCRIPTION

Figure 1:
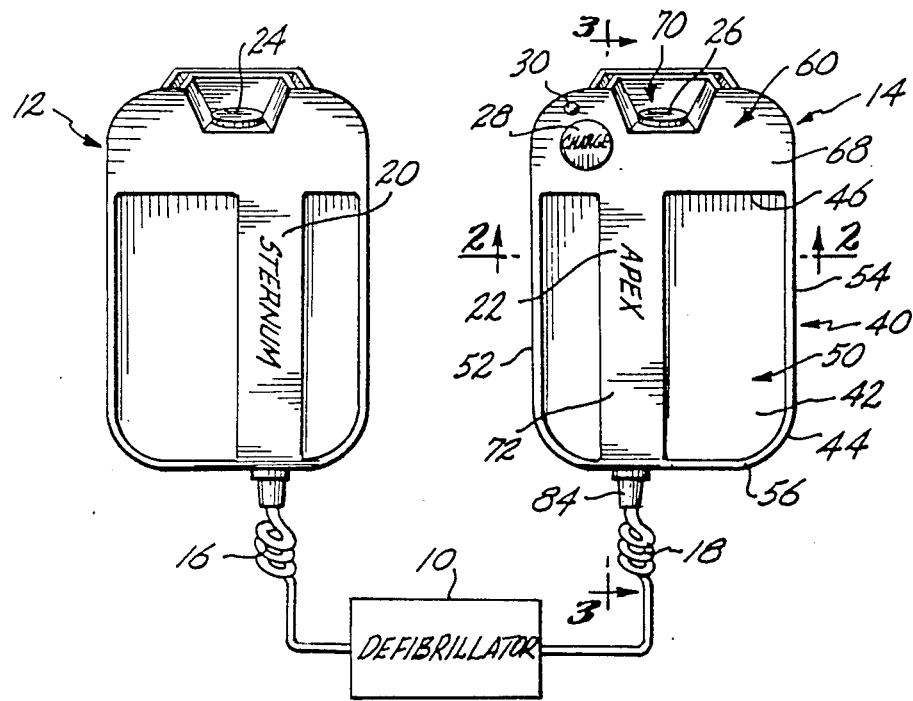
FIG. 1 is a plan view of left and right-handed electrodes according to the present invention.

FIG. 1 illustrates defibrillator 10 to which sternum electrode 12 and apex electrode 14 are connected by cables 16 and 18, respectively. Sternum electrode 12 is adapted to be held in an operator's left hand and applied to a patient at the sternum position. Apex electrode 14 is adapted to be held in the operator's right hand and applied to the patient at the apex position. Labels 20 and 22 are provided on electrodes 12 and 14 respectively to facilitate proper electrode placement. Sternum electrode 12 includes discharge switch 24, and apex electrode 14 includes discharge switch 26, charge switch 28 and charge indicator 30. To deliver an electric shock, the operator may first actuate charge switch 28 to charge the energy storage means of the defibrillator. While the energy storage means is charging, charge indicator 30 blinks on and off. When the energy storage means is fully charged, charge indicator 30 remains steadily on. At that time, the operator can deliver a defibrillation shock to the patient by simultaneously depressing discharge switches 24 and 26. It is to be understood that the present invention includes all medical instruments that include a pair of hand-held electrodes that should preferably be held by an operator with particular electrodes in particular hands.

Electrodes 12 and 14 are connected to the defibrillator such that when a defibrillation discharge is delivered, sternum electrode 12 is predominantly negative with respect to apex electrode 14. Proper placement of the electrodes on the patient is facilitated by labels 20 and 22. Proper placement is further facilitated by the physical construction of the electrodes. As described more fully below, sternum electrode 12 is adapted such that it can be readily gripped by an operator's left hand with the operator's thumb adjacent discharge switch 24, but such that it is difficult for an operator to grip and use the sternum electrode with his or her right hand. Apex electrode 14 is essentially the mirror image of sternum electrode 12, such that the apex electrode can readily be gripped and used with the right hand but not with the left hand. During use of the defibrillator, the operator will normally be facing the patient, such that the patient's sternum position is to the operator's left and the patient's apex position is to the operator's right. The left and right-handedness of electrodes 12 and 14, respectively, therefore facilitate use of the electrodes with the appropriate polarity.

Figure 2:
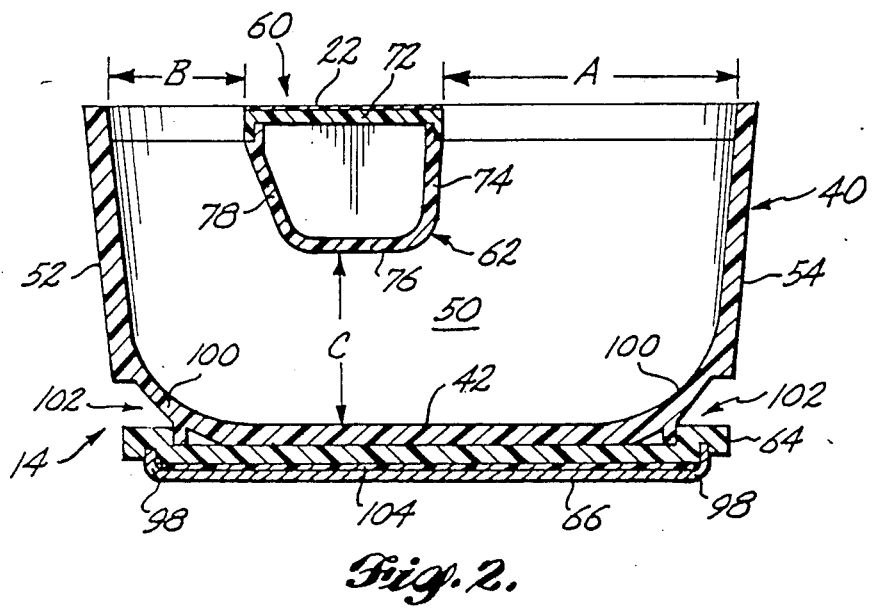
FIG. 2 is a cross-sectional view taken along the line 2—2 of FIG. 1.
Figure 3:
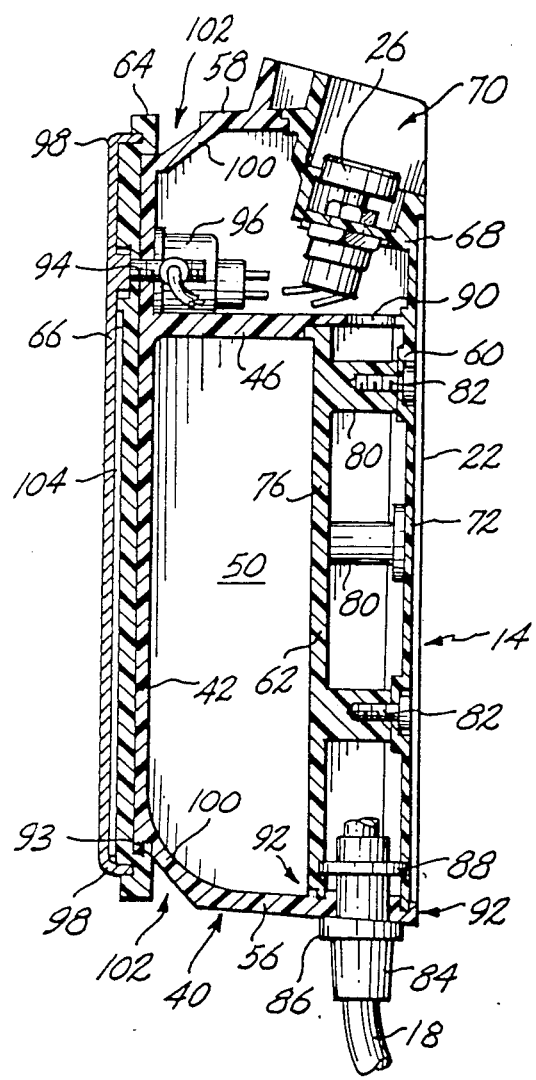
FIG. 3 is a cross-sectional view taken along the line 3—3 of FIG. 1.

Referring now to FIGS. 1-3, electrode 14 comprises housing 40 that includes base 42, upstanding U-shaped rim 44 and upstanding divider 46 (FIG. 3) that combine to define cup-shaped recess 50. Rim 44 comprises sidewalls 52 and 54 and end wall 56. The forward end of housing 40 includes upstanding support 58. Electrode 14 further comprises cover plate 60, handle 62, retainer plate 64 and electrode element 66. Cover plate 60 includes forward section 68 that includes indentation 70 in which discharge switch 26 is mounted, and rearwardly extending handle cover 72. Indentation 70 is appropriately dimensioned to receive an operator's thumb.

Handle 62 includes essentially vertical side 74, lower side 76, angled side 78, and a plurality of posts 80 upstanding from lower side 76. Handle 62 is secured to handle cover 72 by means of bolts 82 that extend through the handle cover and are received within threaded openings in posts 80. The heads of bolts 82 are countersunk into handle cover 72 and covered with label 22. Cable 18 includes strain relief 84 that may be integrally molded to the outer cable cover. Strain relief 84 includes stop 86 for engaging the outer surface of end wall 56, and retainer key 88 for engagement in slots in handle 62 and handle cover 72. The wires (not shown) comprising cable 18 extend through the passage between handle 62 and handle cover 72, posts 80 being offset laterally in alternating fashion to facilitate passage of such wires. The wires exit from forward end 90 of the handle/handle cover passage and make appropriate connections to discharge switch 26, charge switch 28 and charge indicator 30. The wires also connect to high voltage terminal 96 for connection to electrode element 66, as described below.

The assembly comprising handle 62, cover plate 60 and cable 18 is secured to housing 40 by tab/slots 92 at the rearward end of the electrode and by bolts (not shown) at the forward end of the electrode. When so secured, handle 62 is positioned as indicated in FIG. 2, with a comparatively large clearance A between handle 62 and sidewall 54, a comparatively small clearance B between handle 62 and sidewall 52, and an intermediate clearance C between handle 62 and base 42. The dimensions A, B and C are selected such that an operator's hand can be accommodated in recess 50, with the base of the fingers and/or the upper palm received between the handle and sidewall 54, and with the tips of the fingers received between the handle and sidewall 52. However dimension B is selected to be small enough so that it is at least difficult for most persons to pick up electrode 14 by first passing their fingers through the opening formed between sidewall 52 and the handle. In particular, dimension B is chosen to be too small to permit passage of the knuckles and palm of the hands of most operators. Therefore to use electrode 14 such that the fingers grip handle 62 and the thumb is adjacent discharge switch 26, an operator must use his or her right hand. Sternum electrode 12 is essentially the mirror image of apex electrode 14, and is therefore similarly adapted for left-handed use by an operator.

Retainer plate 64 is secured to the bottom of base 42 of the electrode by tab/indent arrangement 93 at the rearward end of the base, and by conducting pin 94 adjacent the forward end of the base. Conducting pin 94 extends through openings in base 42 and in retainer plate 64, and serves to connect electrode element 66 to high-voltage terminal 96 that is positioned in the enclosure just forward of divider 46. High-voltage terminal 96 is electrically connected to discharge switch 26 and cable 18 by appropriate connections (not shown). Electrode element 66 is secured to retainer plate 64 by adhesive 104, the edges 98 of electrode element 66 being received in corresponding recesses around the periphery of the retainer plate. Electrode element 66 is therefore spaced inwardly from the outer edges of retainer plate 64. The lower end of housing 40 immediately above base 42 includes inwardly angled sections 100, resulting in formation of recess 102 around the edges of the electrode just above retainer plate 64. In some embodiments, a magnet or other position sensing means may be positioned in recess 102 adjacent end wall 56 to enable the defibrillator to sense that the electrodes have been stowed on the outer defibrillator housing. Recesses 102 function in combination with recess 50 and with the inward spacing of electrode element 66 from the outer edges of retainer plate 64 to isolate electrode element 66 from the operator's hand, to protect the operator from electric shock that could otherwise occur if, for example, conductive gel were to spill down one side of the electrode. Recesses 102 may also be used to facilitate stowing the electrodes to the defibrillator.

While the preferred embodiments of the invention have been illustrated and described, it should be understood that variations will be apparent to those skilled in the art. Accordingly, the invention is not to be limited to the specific embodiments illustrated and described, and the true scope and spirit of the invention are to be determined by reference to the following claims.

The embodiments of the invention in which an exclusive property or privilege is claimed are defined as follows:

1. A medical instrument comprising first and second electrodes and means for applying an electric shock to a patient through the electrodes, each electrode comprising:
   an elongated member adapted for gripping by the fingers of an operator's hand;
   an actuator positioned adjacent one end of the elongated member;
   an electrode element responsively connected to the actuator, the electrode element including means for receiving and transferring electrical energy; and
   blocking means positioned adjacent one side of the elongated member;
   the blocking means of the first electrode including means to hinder the operator from gripping the elongated member with the operator's right hand and simultaneously positioning the thumb of the right hand adjacent the actuator, the blocking means of the second electrode including means to hinder the operator from gripping the elongated member with the operator's left hand and simultaneously positioning the thumb of the left hand adjacent the actuator, whereby the first and second electrodes are adapted for left and right-handed use, respectively.

2. The medical instrument of claim 1, wherein each blocking means comprises means forming a blocking surface that extends generally parallel to the elongated member.

3. The medical instrument of claim 1, wherein each blocking means comprises means forming a depression having first and second sidewalls, the first sidewall comprising the blocking surface and the second sidewall being positioned with respect to the elongated member such that the operator's hand can be accommodated between the second sidewall and the elongated member.

4. The medical instrument of claim 3, wherein each elongated member comprises a handle spanning the depression in a direction parallel to the first and second sidewalls, such that when the elongated member is gripped by the fingers of the operator's hand, said fingers are received in the depression.

5. The medical instrument of claim 4, wherein each means forming a depression comprises a body, the body comprising the first and second sidewalls and a bottom wall extending between the first and second sidewalls, the electrode element of each electrode underlying the bottom wall.

6. The medical instrument of claim 5, wherein each body is shaped so as to form a lateral recess around a substantial portion of the periphery of the electrode.

7. The medical instrument of claim 4, wherein each means forming a depression comprises a housing, the housing comprising the first and second sidewalls and a base extending between the first and second sidewalls, the electrode further comprising a retainer plate underlying the base, the electrode element underlying the retainer plate.

8. The medical instrument of claim 7, wherein each retainer plate and housing are shaped so as to form a lateral recess around a substantial portion of the periphery of the electrode.

9. The medical instrument of claim 8, wherein each lateral recess is formed at the junction between the retainer plate and the housing, and wherein each retainer plate has a greater lateral extent than the associated electrode element.

* * * * *